United States Patent
Wackym

(10) Patent No.: US 10,338,091 B2
(45) Date of Patent: Jul. 2, 2019

(54) CONCUSSION DETECTION AND COMMUNICATION SYSTEM

(71) Applicant: Ashton Wackym, Portland, OR (US)

(72) Inventor: Ashton Wackym, Portland, OR (US)

( * ) Notice: Subject to any disclaimer, the term of this patent is extended or adjusted under 35 U.S.C. 154(b) by 974 days.

(21) Appl. No.: 13/763,105

(22) Filed: Feb. 8, 2013

(65) Prior Publication Data

US 2014/0052405 A1     Feb. 20, 2014

Related U.S. Application Data

(60) Provisional application No. 61/596,662, filed on Feb. 8, 2012.

(51) Int. Cl.
| | |
|---|---|
| *G01P 15/00* | (2006.01) |
| *A61B 5/00* | (2006.01) |
| *G01P 15/18* | (2013.01) |
| *A42B 3/04* | (2006.01) |
| *G06F 19/00* | (2018.01) |

(52) U.S. Cl.
CPC .......... *G01P 15/00* (2013.01); *A61B 5/6803* (2013.01); *A42B 3/046* (2013.01); *A61B 2562/0219* (2013.01); *G01P 15/18* (2013.01); *G06F 19/3481* (2013.01)

(58) Field of Classification Search
CPC .................................. G01P 15/00; G01P 15/18
See application file for complete search history.

(56) References Cited

U.S. PATENT DOCUMENTS

| | | | |
|---|---|---|---|
| 5,383,363 A | 1/1995 | Kulmaczewski | |
| 5,546,609 A | 8/1996 | Rush, III | |
| 5,592,401 A * | 1/1997 | Kramer | A63B 69/3608 340/524 |
| 5,621,922 A | 4/1997 | Rush, III | |
| 5,978,972 A | 11/1999 | Stewart et al. | |
| 6,826,509 B2 | 11/2004 | Crisco, III et al. | |
| 7,512,515 B2 | 3/2009 | Vock et al. | |
| 7,635,379 B2 | 12/2009 | Callahan et al. | |
| 2005/0177929 A1 | 8/2005 | Greenwald et al. | |
| 2006/0074338 A1 | 4/2006 | Greenwald et al. | |
| 2008/0197024 A1* | 8/2008 | Simpson | A61B 5/14542 205/778 |
| 2008/0284650 A1 | 11/2008 | MacIntosh et al. | |
| 2010/0102970 A1 | 4/2010 | Hertz | |
| 2010/0191356 A1* | 7/2010 | Wehrenberg | G06F 1/1616 700/94 |
| 2010/0198453 A1* | 8/2010 | Dorogusker | A63B 24/0062 701/31.4 |

(Continued)

OTHER PUBLICATIONS

Bjontegard, Contextually Intelligent Communication Systems and Processes, U.S. Appl. No. 61/709,710, Oct. 10, 2012 (Year: 2012).*

*Primary Examiner* — Stephanie E Bloss
*Assistant Examiner* — Lisa E Peters
(74) *Attorney, Agent, or Firm* — Kolisch Hartwell, P.C.

(57) ABSTRACT

A concussion detection and communication system is described. In some examples a concussion data module may be worn by one or more subjects. Each concussion data module may include multiple accelerometers and may communicate data signals wirelessly to a base unit. Upon determining that the base unit is not within effective communication range, a concussion data module may relay signals to the base unit through another concussion data module.

20 Claims, 9 Drawing Sheets

(56) References Cited

U.S. PATENT DOCUMENTS

| | | | |
|---|---|---|---|
| 2011/0098934 A1 | 4/2011 | Hubler et al. | |
| 2011/0181419 A1* | 7/2011 | Mack | A42B 3/046 |
| | | | 340/573.1 |
| 2011/0215931 A1* | 9/2011 | Callsen | F41H 1/04 |
| | | | 340/573.1 |
| 2011/0218756 A1 | 9/2011 | Callsen et al. | |
| 2011/0231145 A1 | 9/2011 | Chen | |
| 2011/0234384 A1* | 9/2011 | Agrawal | G09B 21/009 |
| | | | 340/10.5 |
| 2011/0246123 A1 | 10/2011 | DelloStritto et al. | |
| 2011/0295547 A1 | 12/2011 | Asada et al. | |
| 2012/0004882 A1 | 1/2012 | Sheynblat | |
| 2012/0075095 A1* | 3/2012 | Howard | G08B 13/1427 |
| | | | 340/539.12 |
| 2012/0077440 A1 | 3/2012 | Howard et al. | |
| 2012/0223833 A1* | 9/2012 | Thomas | G06F 19/3418 |
| | | | 340/539.12 |

* cited by examiner

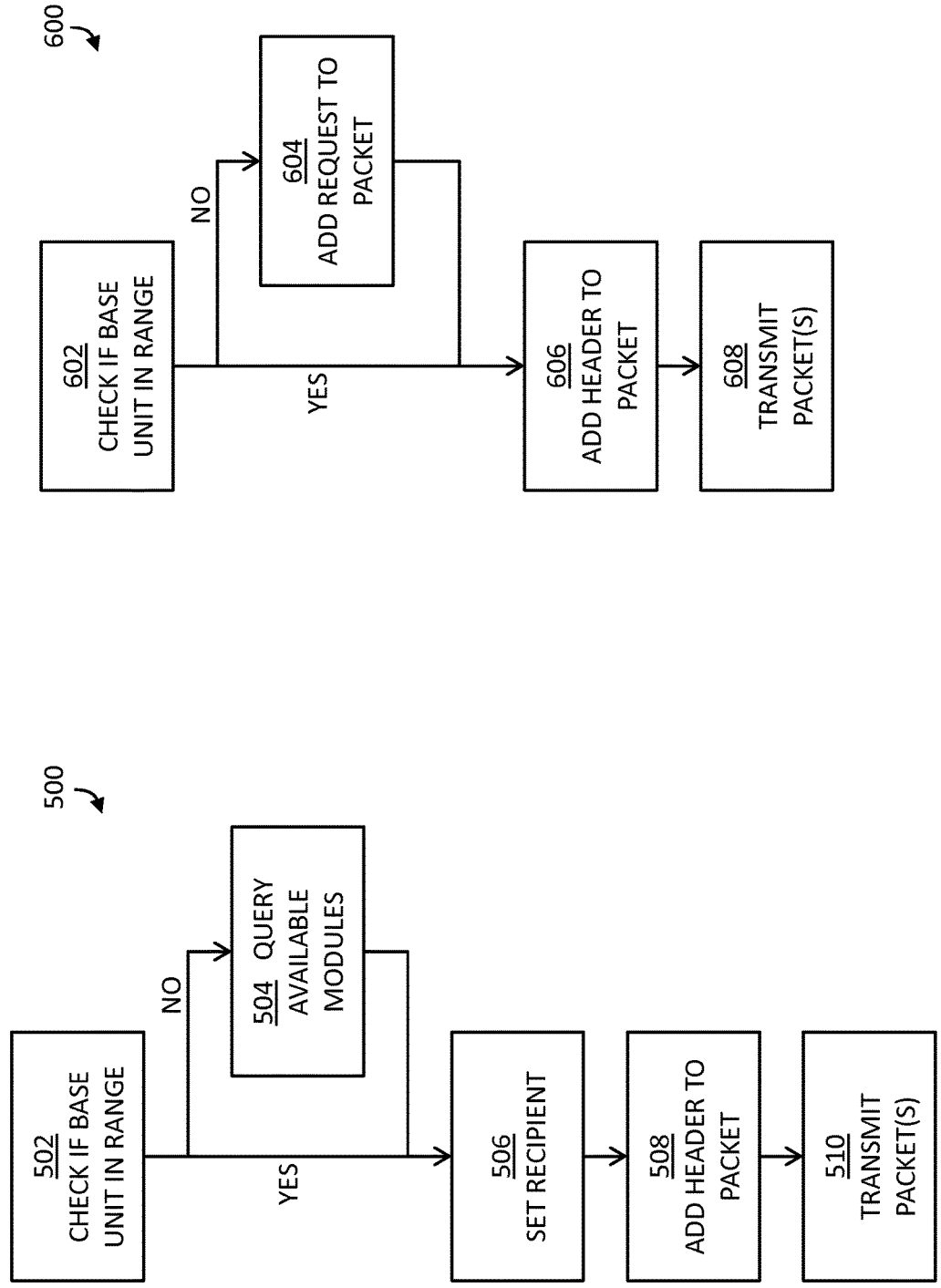

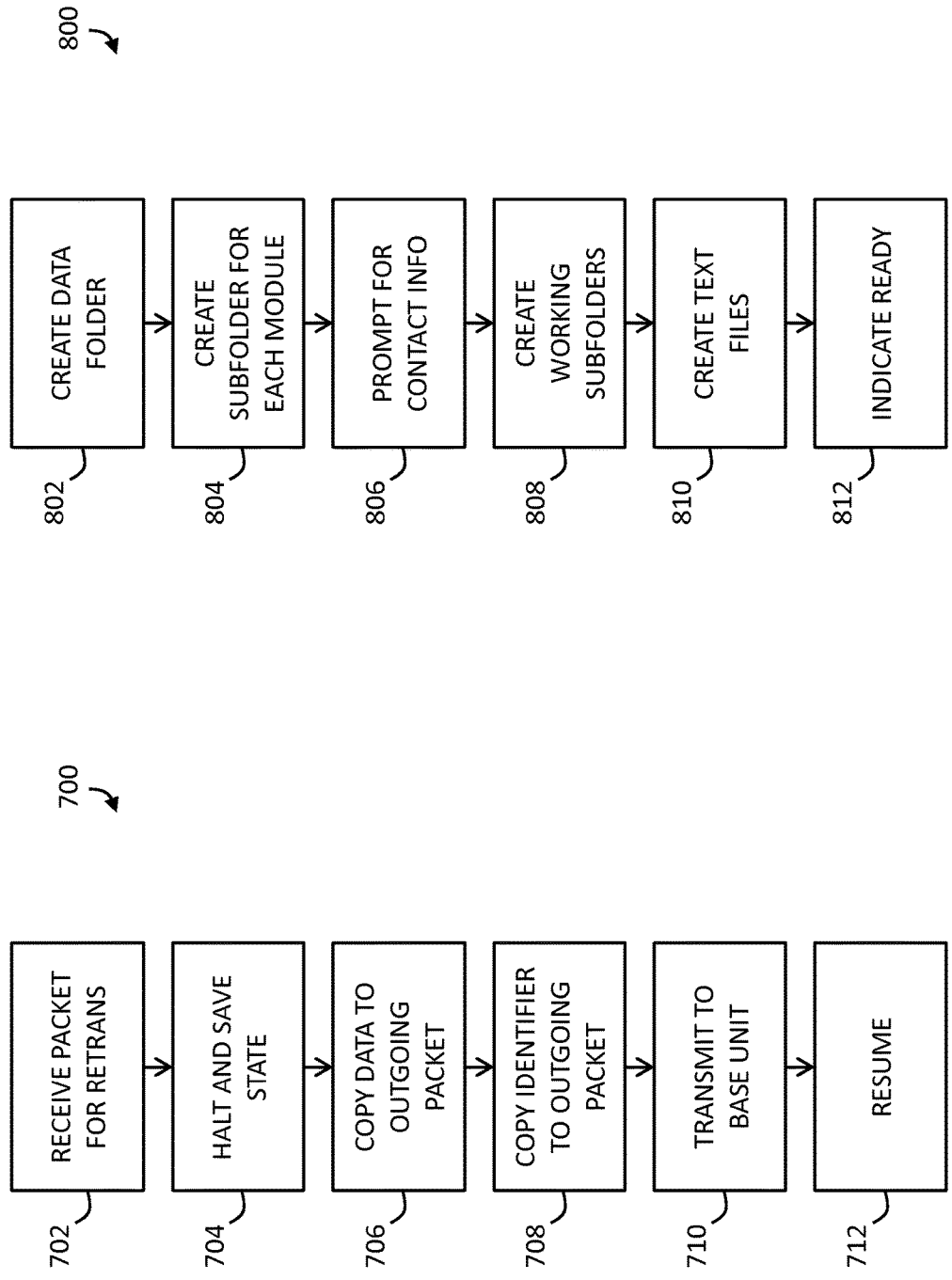

CONCUSSION DETECTION AND COMMUNICATION SYSTEM

CROSS REFERENCE TO RELATED APPLICATION

This application claims priority under 35 U.S.C. § 119(e) to U.S. Provisional Patent Application Ser. No. 61/596,662, filed Feb. 8, 2012, which is incorporated herein by reference in its entirety for all purposes.

FIELD

This disclosure relates to wearable sports equipment and to concussion detection systems for use during sports and other activities in which concussions may occur.

INTRODUCTION

Concussions have always plagued the lives of professional and amateur athletes alike. However, the critically damaging and lasting effects of such injuries have not come to the attention of researchers until recently, as revealing studies of post-mortem brains have become available. The horrific consequences of repeated sport-related concussions are still in the process of being recognized by the general population. Experts still do not know everything about the damage concussions cause, nor have effective methods been developed for quantifying and analyzing concussive events across sports and other fields of application. The ability to identify concussions quantitatively and instantaneously lags behind the awareness of a need for such an ability.

In order to recognize concussions on site, an instantaneous and quantitative concussion detection system is needed to analyze and display the concussive forces an athlete undergoes.

Conversely, systems for concussion detection through qualitative analysis leave much of the interpretation of symptoms up to the observer. This subjective analysis leads to errors in judgment from coaches and players alike, who often feel pressure to keep athletes in the game even after sustaining a significant injury.

BRIEF SUMMARY

In some examples, a concussion detection and communication device may include a first electronic module capable of being mounted to a sports helmet. The first electronic module may include a controller, a transmit-receive assembly in communication with the controller, a first three-axis accelerometer and a second three-axis accelerometer each in communication with the controller and configured to communicate respective acceleration data to the controller, and a data storage unit in communication with the controller. The controller may be configured to generate digital data packets, and the data storage unit may be configured to store the digital data packets. Each digital data packet may contain information corresponding to the acceleration data from both of the first and second accelerometers at a certain time. The first electronic module may be operable in a first mode, in which the controller transmits via the transmit-receive assembly a first electromagnetic (EM) signal encoding at least one digital data packet associated with the first electronic module. The first electronic module may be operable in a second mode, in which the processor does not transmit digital data packets associated with the first data module. The transmit-receive assembly of the first electronic module may be capable of receiving a second EM signal transmitted by a second such electronic module, and the controller of the first electronic module may be configured to respond to the received second EM signal by retransmitting data contained in the second EM signal when the second EM signal contains information indicating a retransmission request.

BRIEF DESCRIPTION OF THE DRAWINGS

FIG. 9 is an illustrative method for transmitting data in a concussion data module.

FIG. 10 is another illustrative method for transmitting data in a concussion data module.

FIG. 11 is an illustrative method for retransmitting data in a concussion data module.

FIG. 12 is an illustrative method for initializing a base unit.

DETAILED DESCRIPTION

The present disclosure enables a thorough quantitative analysis of the physical forces that cause concussions, and simultaneously facilitates a reduction in pressured or erroneous judgment. A concussion detection and communication system is described in which one or more concussion data modules are associated with an individual player-subject for collecting and communicating data associated with accelerative and concussive events experienced by the subject. For example, each data module may be programmed to calculate both linear and angular acceleration vectors, and to compare those results to threshold values that may indicate a need for further medical analysis or monitoring. A concussion data module according to the present disclosure may be easily transferred between helmets and head mounting devices. In addition to the data modules, a concussion detection and communication system may include a base unit configured to receive information communicated from the data modules in real time, and to perform additional analysis and processing. For example, the base unit may include a personal computer, and may store data, display charts of acceleration information for each subject involved, and facilitate alerts of healthcare personnel, relatives, and/or coaches either directly or remotely. If more than one data module is associated with a given subject, the base unit may also coordinate comparative and contextual analysis based on the multiple data streams per subject.

In some examples, the data modules may communicate wirelessly with the base unit, and may communicate with each other, for example to relay signals to the base unit if not in range to communicate directly. For example, a first data module that is out of range to the base unit may relay a communication to the base unit through a second data module that is within range of both the first module and the base unit. In some examples, the base unit may transmit signals and information to one or more data modules in addition to receiving information from them.

Figure 1:
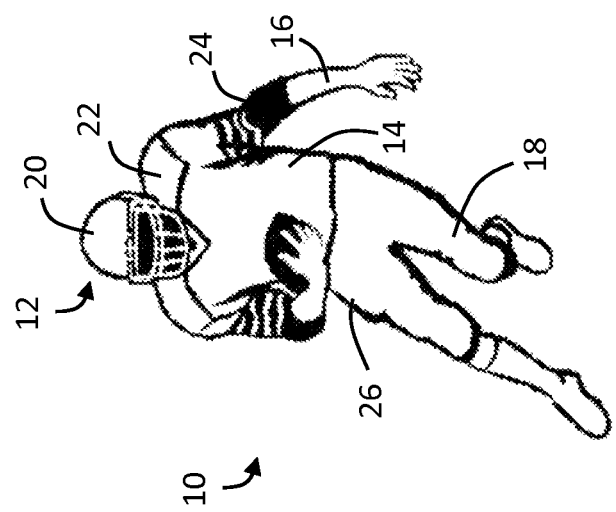
FIG. 1 shows an example of a user of an illustrative concussion detection system.

A concussion data module may detect acceleration of one or more body parts of the subject and wirelessly transmit acceleration data to another device such as a base unit for further analysis. FIG. 1 shows an illustrative player-subject generally indicated at 10. Subject 10 may be a human athlete participating in a sport in which collisions occur between participants and/or between a participant and inanimate objects such as the ground or a moving or non-moving object, such as in the sport of American football. Sports such as football, hockey, auto racing, lacrosse, and/or boxing may frequently include collisions and therefore a concussion risk to the subject/participant. As shown in FIG. 1, subject 10 may include body parts such as a head 12, a torso 14, two arms 16, and two legs 18. Subject 10 may wear protective equipment on one or more of these body parts, such as a helmet 20 on head 12, shoulder pads 22, elbow pads 24, and/or leg pads 26. One or more concussion data modules may be associated with subject 10, and may, for example, be disposed on or in pieces of protective equipment. In some examples, one concussion data module may be attached to helmet 20, or directly to head 12, or by using other wearable equipment such as an elastic headband. In other examples, an additional concussion data module may be attached to shoulder pads 22 at a location on or near torso 14. In some examples, a concussion data module may be firmly and releasably attached to the helmet. In other examples, a concussion data module may be a unitary part of the helmet or other equipment.

Figure 2:
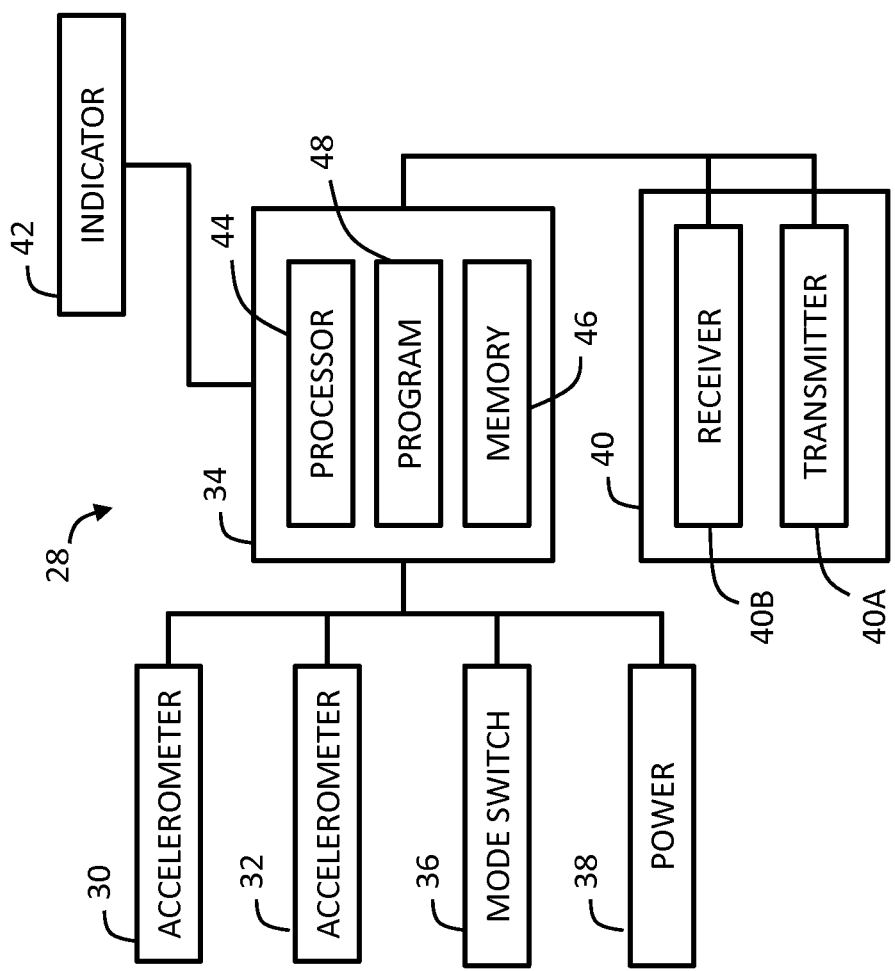
FIG. 2 is a block diagram of an illustrative concussion data module.

FIG. 2 shows a block diagram of an illustrative concussion data module 28. Concussion data module 28 may be any suitable device configured to be mountable to the body of a subject, to detect acceleration, to calculate linear and rotational acceleration information, and to communicate the acceleration information to a remotely located receiving device. In some examples, concussion data module 28 may be configured to receive communicated information and to take action in response to the received information. In the example depicted in FIG. 2, concussion data module 28 includes a first accelerometer 30, a second accelerometer 32, a controller 34, a mode switch 36, a power supply 38, a transmit/receive unit 40, and an indicator 42.

Accelerometers 30 and 32 may each be any suitable device configured to detect and measure acceleration on one or more axes and to communicate the resulting data in digital form to controller 34. In the example shown, each accelerometer may be a three-axis accelerometer known in the industry and may be capable of measuring and communicating acceleration data at a rate of over one thousand times per second. Accelerometers 30 and 32 may produce acceleration values for the x, y, and z axes. Each accelerometer produces acceleration information for any object to which the accelerometer is attached. High frequency of acceleration data generation may be required due to the nature and duration of concussive events. In this example, the accelerometers pass the acceleration data unaltered to the controller as the data is generated.

Controller 34 may include a processor 44 and a data storage unit 46, and may be any suitable computer processing and memory device configured to receive data from accelerometers 30 and 32, to calculate resulting vectorized linear and angular acceleration for each data point, to store at least a portion of the data and/or vector results, and to coordinate the communication of those results in a manner based on a selected mode as indicated by mode switch 36. Processor 44 may be configured to execute computer program instructions 48 to calculate acceleration parameters based on the data received from the accelerometers. For example, a linear acceleration vector for each of the accelerometers may be calculated from the respective x, y, and z values, resulting in one overall linear acceleration value for each accelerometer. In addition, utilizing two accelerometers spaced from each other allows rotational or angular acceleration to be calculated, for example, as follows:

$$Az = \frac{(a_{y2} - a_{y1})Px + (a_{x2} - a_{x1})Py}{Px^2 + Py^2}$$

$$Ay = \frac{(a_{z2} - a_{z1})Px + (a_{x2} - a_{x1})Pz}{Px^2 + Pz^2}$$

$$Ax = \frac{(a_{y2} - a_{y1})Pz + (a_{z2} - a_{z1})Py}{Pz^2 + Py^2}$$

Where Az, Ay, and Ax are angular accelerations in the respective z, y, and x directions, Px, Py, and Pz are the distances in the x, y and z directions between accelerometers, and ax, ay, and az are the linear accelerations. Note that ax1 represents the x-axis acceleration on one accelerometer and ax2 represents the x-axis acceleration on the other accelerometer. Alternatively, a formula such as the following may be used (with similar formulas for the other axes):

$$Az = \frac{a_{x2} - a_{x1}}{2Px} - \frac{a_{y2} - a_{y1}}{2Py}$$

An overall angular acceleration vector may be calculated from the individual angular accelerations on the respective axes.

The resulting values may be stored in data storage unit 46, along with identifying information and a time stamp, which may be determined from an onboard clock (not shown) or from an external clock signal. Processor 44 may also execute instructions of program 48 to compare each value to a predetermined or user-specifiable threshold, and store the result along with the data point. For example, each linear value may be compared to a linear threshold, and each angular value may be compared to an angular threshold. In addition, there may be two types of each threshold: a lower and an upper threshold, also known as a mild and a severe threshold, respectively.

In some examples, a certain number of events exceeding the lower threshold may indicate that medical attention is needed. On the other hand, exceeding an upper threshold even once may indicate a need for medical attention. Processor 44 may be programmed to compare the acceleration values to all such thresholds, to add corresponding information to the data records, and to keep track of how many times each threshold has been exceeded. Data storage unit 46 may allow storage of a finite amount of data, acting as a buffer corresponding to a set amount of time based on the rate of data generation.

Mode switch 36 may be any suitable component or virtual switch configured to be selectable between two or more states. In some examples, mode switch 36 may be a physical switch operable to change a persistent variable stored by the controller. In some examples, the variable itself may be referred to as the mode switch. In a first state, switch 36 may indicate to processor 44 that the processor should operate in a first mode, and in a second state, switch 36 may indicate to processor 44 that the processor should operate in a second mode.

The first mode may include continuous transmission of the acceleration information calculated by controller 34. By continuous, it is meant that a repeated and periodic transmission of the contents of data storage unit 46 may be performed. For example, controller 34 may transmit accumulated data via transmit/receive module 40 one time each half-second. In this example, if a data generation rate were 1,000 data points per second and data were transmitted once per half-second, each data transmission would include 500 data points. Each data point, or packet, in this case would include the respective linear and angular acceleration values calculated by the processor, along with corresponding time, identification, and threshold information. In some examples, the data in data storage unit 46 may be deleted or overwritten once it has been transmitted. In other examples, data may accumulate in data storage unit 46 until a predetermined limit is met, at which point the oldest information may be deleted to make room for the newest on a first-in-first-out (FIFO) basis.

The second mode may include event-based transmission. In the second mode, acceleration values and other information may accumulate in data storage unit 46 as described above. However, in the second mode, communication of the data points may occur only upon a triggering event. For example, a triggering event may include exceeding an upper threshold, exceeding a lower threshold, and/or exceeding a lower threshold a certain number of times. If a triggering event occurs, the concussion data module may automatically transmit the contents of the data storage unit. In some examples, this transmission is accomplished by switching the concussion data module into the first mode. After the data is transmitted, the module may remain in the first mode, or may revert to the second mode.

A third state of switch 36 may indicate that data should be transmitted only on demand. Transmission on demand may be accomplished by receiving a transmit command from the base unit, and transmitting the contents of data storage unit 46 in response. In some examples, a demand to transmit may be provided by a user directly to the concussion data module, either through a physical switch or button or through any other suitable method. In other examples, transmission on demand may be incorporated into one or both of the first and second modes.

Power supply 38 may include any suitable energy storage device connectable to provide electrical power to other components of concussion data module 28. For example, power supply 38 may include a DC battery, a capacitor, an ultracapacitor, and/or a fuel cell. Power supply 38 may be rechargeable.

Transmit/receive unit 40 may be any suitable device configured to communicate electromagnetic (EM) signals to and/or from controller 34. For example, a transmitter 40A and a receiver 40B may be configured to communicate information-containing digital signals wirelessly with one or more external devices. Transmit/receive unit 40 may be configured to operate in the Ultra High Frequency (UHF) band.

Indicator 42 may be any suitable visual and/or audible indicator configured to respond to a signal from controller 34. For example, indicator 42 may emit light or sound in response to an event or mode. Indicator 42 may include one or more of the following: lamp, LED, flag, buzzer, speaker, flasher, siren, beeper, and/or chime.

Figure 3:
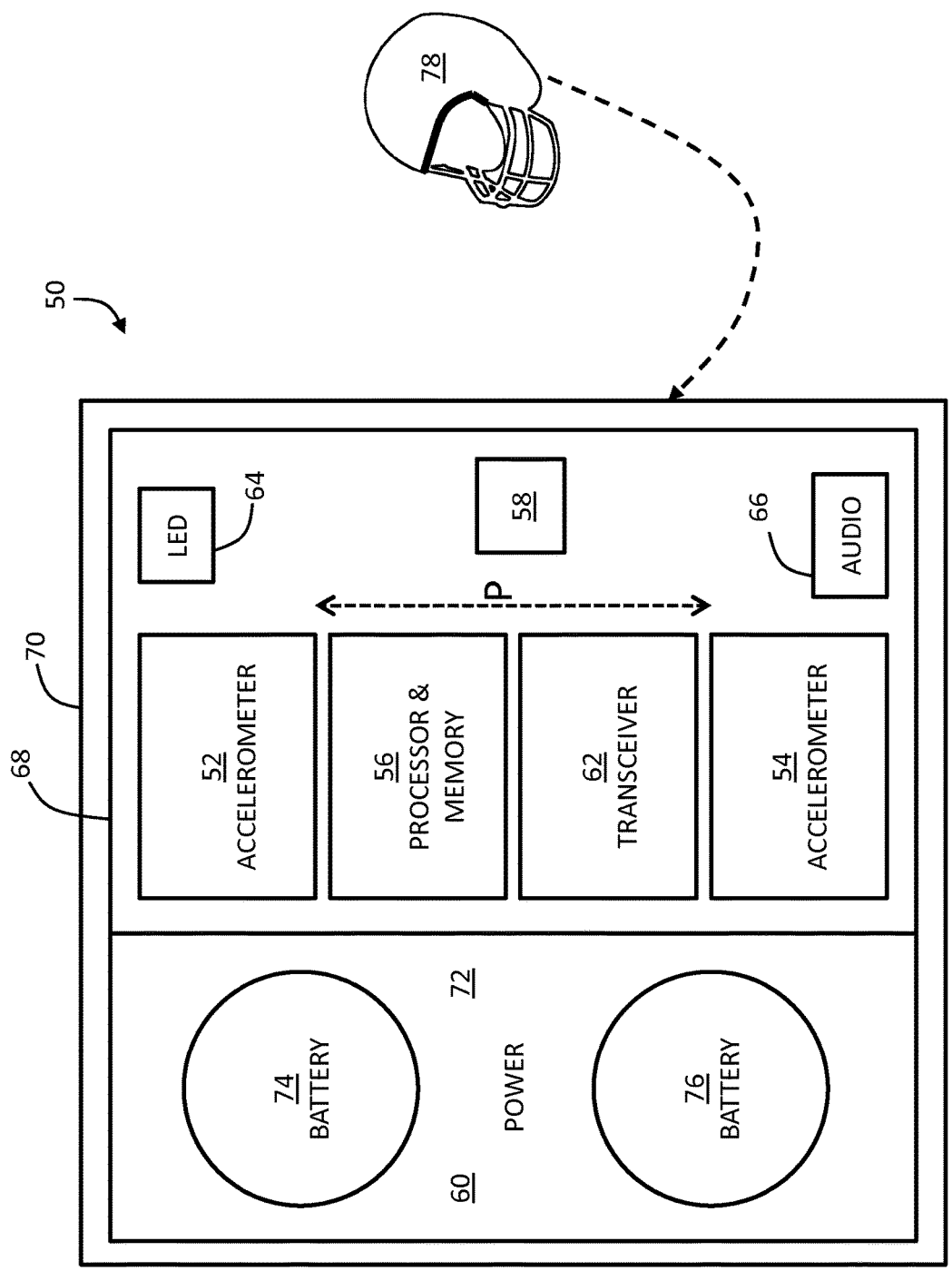
FIG. 3 is a schematic diagram of an illustrative concussion data module.

Turning now to FIG. 3, a schematic view of an illustrative concussion data module 50 is shown, indicating a physical arrangement of the various components. Concussion data module 50 may be an example of concussion data module 28. Accordingly, concussion data module 50 may include a first accelerometer 52, a second accelerometer 54, a processing and memory unit 56, a mode switch 58, a power supply 60, a transmitter/receiver unit 62, and indicators 64 and 66. The various components may be disposed on a mounting board 68, and may be encased in an enclosure 70.

First and second accelerometers 52 and 54 may each be an example of accelerometers 30 and 32, and may include any suitable accelerometer configured to communicate real time three-axis acceleration data to processing and memory unit 56. First accelerometer 52 may be spaced a distance P from second accelerometer 54 in order to facilitate calculation of angular or rotational acceleration as described above.

Processing and memory unit 56 may be an example of controller 34, and may include any suitable device configured to process and store information communicated from accelerometers 52 and 54 and to coordinate communication of information with other devices via transmitter/receiver unit 62. In some examples, processing and memory unit 56 may include an Arduino® microcontroller.

Mode switch 58 may be an example of mode switch 36, and may include any suitable electrical or electronic, momentary-type switch configured to indicate to processing and memory unit 56 that the system should switch from one mode to another mode, as described above regarding switch 36. For example, switch 36 may be a pushbutton. In some examples, processing and memory unit 56 may be configured to receive a mode-switching signal from either switch 58 or a virtual toggle signal received through transmitter/receiver unit 62, or both, and may also toggle between modes in response to certain events.

Power supply 60 may be an example of power supply 38, and may include one or more portable batteries to provide electrical power to other components of concussion data module 50. For example, power supply 60 may include a detachable battery mounting board 72 and two button-type lithium-ion batteries 74 and 76. Batteries 74 and 76 may be rechargeable or may be single-use. For purposes of illustration, two batteries are shown in FIG. 3. However, one battery or more than two batteries may be included. Mounting board 72 may be detachable to facilitate swapping out batteries when power supply 60 is depleted.

Transmitter/receiver unit 62 may be an example of a transmitter/receiver unit 40, and may include any suitable devices configured to transmit and/or receive electromagnetic (EM) signals in the UHF band. For example, transmitter/receiver unit 62 may include an XBee® radio module using the ZigBee protocol.

Indicators 64 and 66 may be examples of indicator 42. Indicator 64 may include an LED lamp, which may light or flash in response to a signal from processing and memory unit 56. For example, processing and memory unit 56 may cause indicator 64 to flash in response to one or more acceleration parameters exceeding a threshold. In other examples, indicator 64 may light or flash to indicate a current mode of the device. Likewise, audio indicator 66 may include a speaker or buzzer device to create an audible indication in response to a signal from processing and memory unit 56. In some examples, a pre-recorded or real-time spoken message may be played through audio indicator 66.

Some or all of the previously discussed components may be mounted to mounting board 68. Mounting board 68 may be any suitable expanse on which components may be arranged and placed in electrical or electronic communication with each other. For example, mounting board 68 may include a solderless breadboard.

Enclosure 70 may be any suitable enclosure configured to contain and protect the components of concussion data module 50 from the environment. For example, enclosure 70 may be a rigid or semi-rigid plastic container. In some examples, enclosure 70 may include a dielectric encapsulant. Components of concussion data module 50 may be enclosed in an enclosure 70 that is sized and shaped such that one or more concussion data modules 50 may be placed securely on or within a piece of personal protective gear such as a helmet 78. As shown in FIG. 1, a helmet 20 such as helmet 78 may be worn on head 12 of subject 10. For discussion purposes, a football helmet is shown in the drawings. However, any suitable helmet or headgear may be used, depending on the sport or activity involved.

Concussion data module 50 may be secured to helmet 78 by any suitable method. For example, concussion data module 50 may be secured inside helmet 78 using adhesive, hook-and-loop fasteners, snaps, clips, screws, bolts, tabs, and/or a suitable pocket or receptacle. In some examples, concussion data module 50 may be releasably secured inside a rear portion of helmet 78 between two adjacent pads. In some examples, one or more additional concussion data modules 50 may be associated with an individual subject. For example, an additional concussion data module 50 may be secured to another piece of personal protective gear such as shoulder pads 22, thereby providing acceleration data regarding torso 14.

Figure 4:
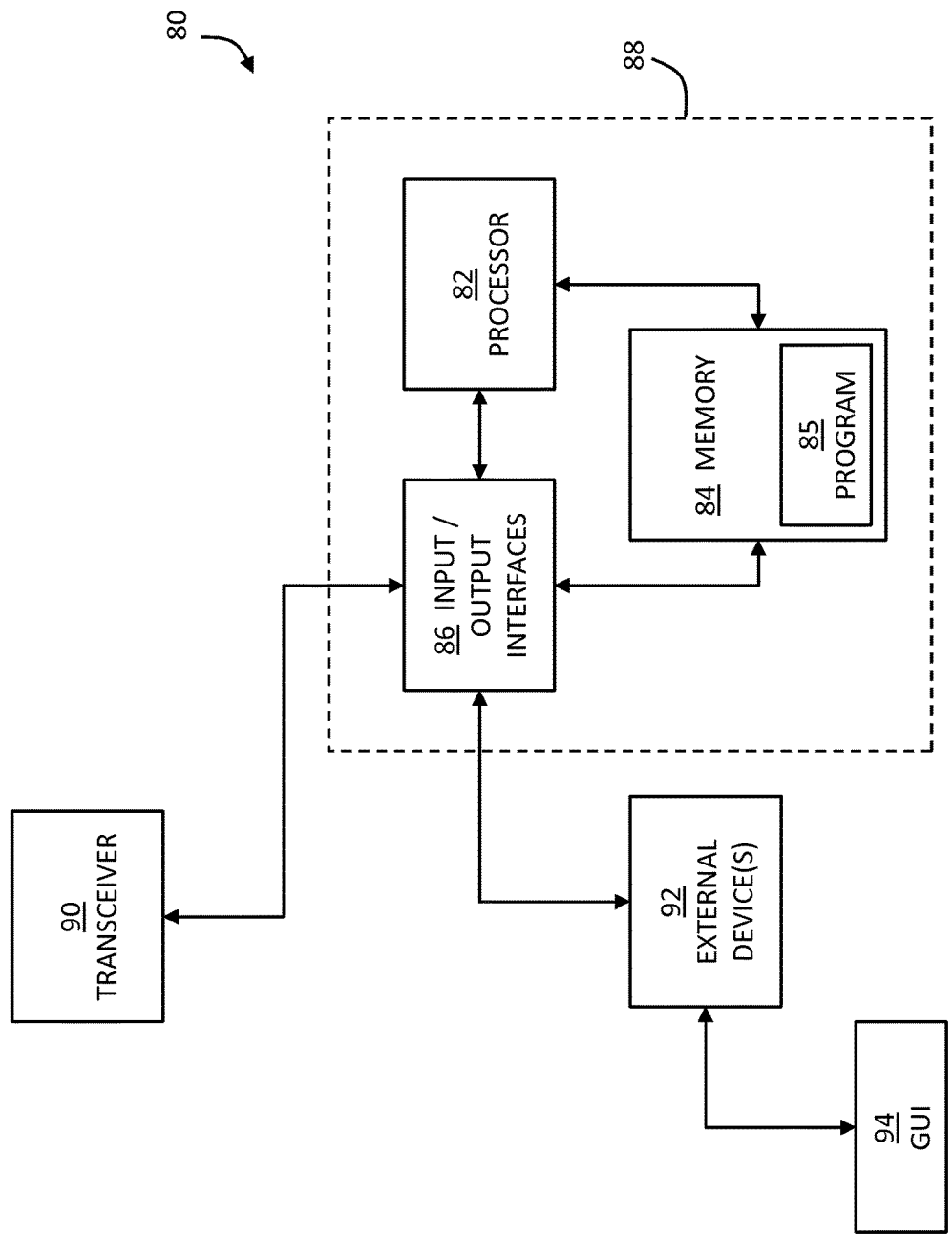
FIG. 4 is a schematic diagram of an illustrative base unit.

FIG. 4 shows a schematic diagram of a base unit 80. Base unit 80 may be any suitable device configured to communicate with one or more concussion data modules such as concussion data module 50, and to further process data received from the concussion data modules. In the example depicted in FIG. 4, base unit 80 includes a processor 82, a memory 84, input/output interfaces 86, a transceiver 90, and external devices 92. Processor 82 may include any suitable digital processor such as a central processing unit (CPU) commonly found in desktop or laptop computers. Memory 84 may include any suitable digital memory storage, such as RAM, ROM, a hard drive, a solid state drive, a working memory, and/or a removable storage device. One or more computer program instructions 85 may be storable in memory 84 for execution by processor 82. Input/output interfaces may include any suitable interface circuitry configured to allow processor 82 and memory 84 to interface with an external device or devices. Taken together, processor 82, memory 84, and input/output interfaces 86 may comprise a typical personal computer (PC) 88 such as a desktop or laptop computer, or a tablet computer.

Transceiver 90 may include any suitable device configured to transmit and/or receive EM signals such as the signals associated with concussion data modules previously described. In some examples, transceiver 90 may include a receiver device configured to receive EM signals in the UHF band and to communicate the information contained in those signals to processor 82 through input/output interfaces 86. In some examples, transceiver 90 may include a transmitter device configured to communicate EM signals in the UHF band, with the signals containing information communicated to the transmitter from processor 82 via input/output interfaces 86. In some examples, a transceiver device may be included, incorporating both the transmitter and the receiver functions. For example, a transceiver 90 may include an XBee® Explorer receiving unit, also known as a "dongle," which may be capable of being plugged into PC 88 through a standard USB port.

External devices 92 may include any suitable electronic devices or peripherals capable of interfacing with PC 88. For example, external devices 92 may include a display, a printer, and/or an external memory. External devices 92 may include a network such as a local area network and/or the Internet. External devices 92 such as a display may be capable of displaying a suitable graphical user interface (GUI) 94 configured to allow a user of base unit 80 to interact with computer program 85.

Figure 5:
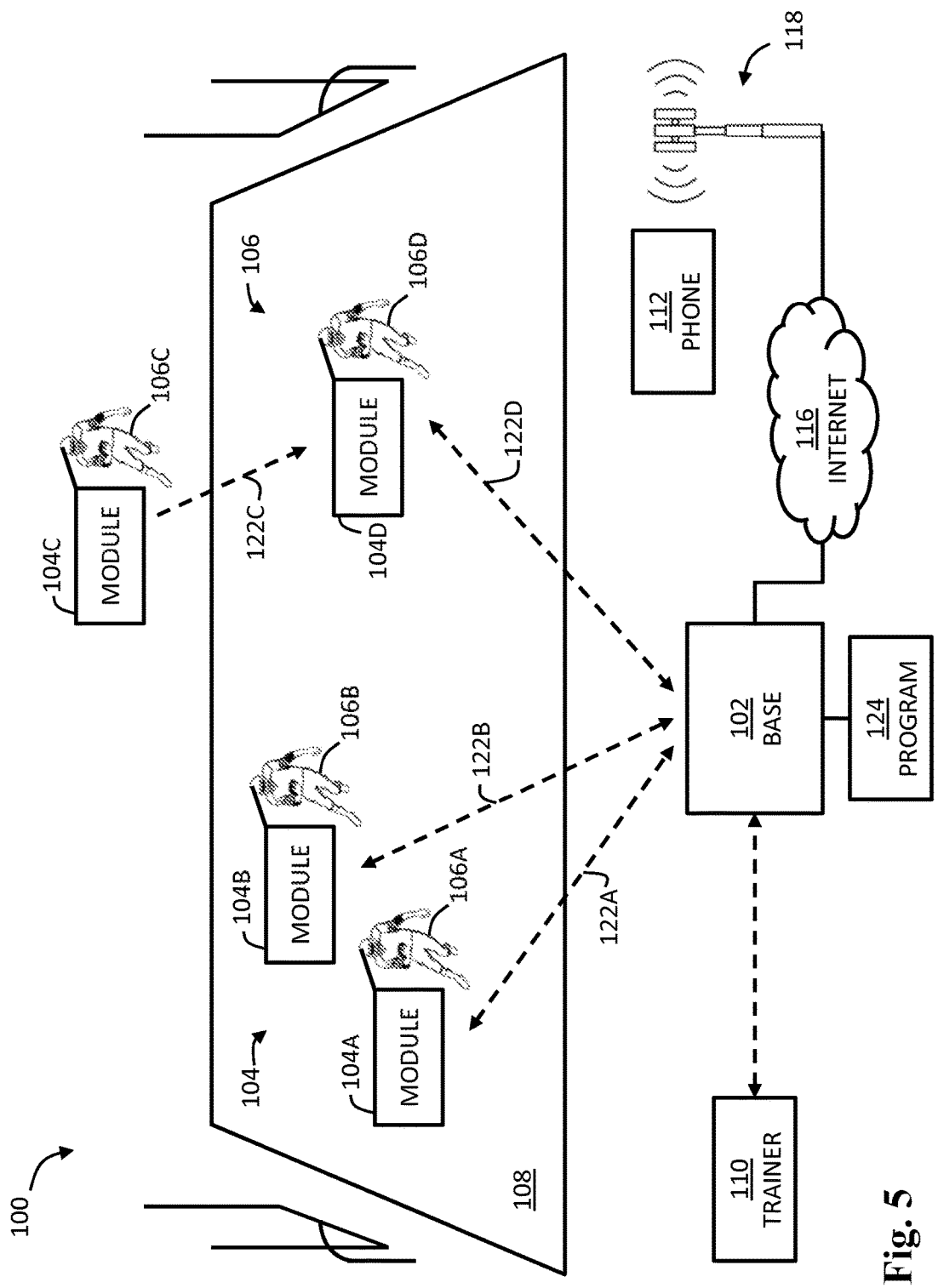
FIG. 5 is a schematic diagram of an illustrative concussion detection system.

Turning to FIG. 5, an illustrative concussion detection system 100 is depicted. In this example, concussion detection system 100 includes a base unit 102 in wireless communication with multiple concussion data modules 104 such as concussion data modules 104A, 104B, 104C, and 104D, respectively associated with individual human subjects 106, such as subjects 106A, 106B, 106C, and 106D, dispersed on and around a field 108. Base unit 102 may be in further communication with additional electronic devices such as a portable pager or computer 110 and/or a cell phone 112.

Base unit 102 may be an example of the previously described base unit 80, and may include a connection 114 to the Internet 116. Connection 114 may include a physical connection such as a cable connected to a cable modem, and/or may include a wireless connection such as through a typical wi-fi router. Internet 116 may be in communication with a cellular telecommunication system 118 via connection 120. Connection 120 may include a voice over internet protocol (VOIP) system, such as Google Voice, capable of sending voice and text-based messages to voice- and/or data-capable devices such as cellular telephone 112.

Base unit 102 may be in communication with the various concussion data modules 104. For example, base unit 102 may be configured to receive any EM signals sent by any of the concussion data modules. Because data may therefore be communicated from more than one source concussion data module, identifying information must be included with the data to allow base unit 102 to associate the data with its source. For example, each concussion data module 104 may have a predetermined numerical or alphanumerical identifier, and may transmit that identifier along with any data originating with that concussion data module. Similarly, data that must be relayed from one concussion data module through another concussion data module before reaching the base unit may retain the identifier of the original source concussion data module to ensure proper association of acceleration data to human subject.

Each concussion data module 104 may have a certain maximum effective range associated with the transmitter, and that range may be on the order of tens or hundreds of meters. Additionally, lower range capabilities may be desired to reduce power consumption and increase battery life. Accordingly, base unit 102 will only receive transmissions from concussion data modules that are within the maximum effective range. Depending on the positions of the player-subjects 106 and the size of the playing field 108, one or more concussion data modules may be out of range from time to time.

Base unit 102 may be configured to send a verification signal to each concussion data module 104 indicating that the base unit is in communication with the respective concussion data module. Each concussion data module 104 may be configured to determine whether it is within range of the base unit by determining if the verification signal from the base unit has been received. In the example shown in FIG. 5, concussion data modules 104A, 104B, and 104D are within range, as indicated by the respective two-way connections shown as dashed lines 122A, 122B, and 122D. However, in this example, concussion data module 104C is beyond maximum effective range, and cannot communicate with base unit 102. In response to a determination that the verification signal from the base unit is not being received, each concussion data module may be configured to broadcast a signal indicating a need for assistance, here shown as a one-way connection 122C. A concussion data module 104 that is within range of both the out-of-range concussion data module 104C and of base unit 102 may then respond with an availability signal. In this example, concussion data module 104D may indicate availability. In some examples, more than one concussion data module may indicate availability, and the out-of-range concussion data module may select one module from the available modules using any suitable method.

Out-of-range concussion data module 104C may relay its data through available concussion data module 104D to base unit 102. To facilitate this relay functionality, each concussion data module 104 may include both receiver and transmitter capabilities, and may be programmed to listen for incoming signals from other concussion data modules, to respond with an availability signal if assistance is requested, and/or to retransmit any signals indicating a need for retransmission. An out-of-range concussion data module 104 may address outgoing data specifically for the concussion data module 104 that has indicated availability and been selected to act as a relay device, allowing other concussion data modules to ignore the transmission. In other examples, a concussion data module 104 finding itself out of range of the base unit may append information to the data being transmitted, the appended information indicating that any concussion data module receiving the transmission should retransmit the data.

Upon receiving the data transmitted and/or retransmitted by concussion data modules 104, base unit 102 may parse and collate the acceleration information into a respective individual file associated with each concussion data module. Chronological acceleration information may thereby by accumulated for each concussion data module 104 and each player-subject 106. This information may be graphed or otherwise presented on a human-readable display. Events such as the exceeding of a threshold may also be presented on the display. Important events may be communicated to one or more persons such as a trainer, doctor, parent, or coach via pager 110 or cell phone 112. For example, a computer program 124 may be an example of a computer program 85, and may be executed to send a text message to a predetermined or user-input cell phone number over a VOIP system using Internet 116.

Accumulated data in the digital files stored in the memory of base unit 102 may be saved for later review or analysis. For example, acceleration data from the files may be used to recreate the path over time taken by a subject 106. This is possible due to the mathematical relationship between acceleration, velocity, and displacement. Because acceleration is the derivative of velocity with respect to time, and the second derivative of position with respect to time, velocity and position information may be determined from the acceleration data. A concussion data module may need to be "reset" or "zeroed" to a known geographical position before collecting the acceleration information, because all acceleration and position calculations will necessarily be relative to a starting point.

Turning now to the methods and algorithms embodied in the various computer programs run by the concussion data modules and base unit, examples of key processes will be described and discussed. The examples described are intended to be illustrative.

Figures 6, 7:
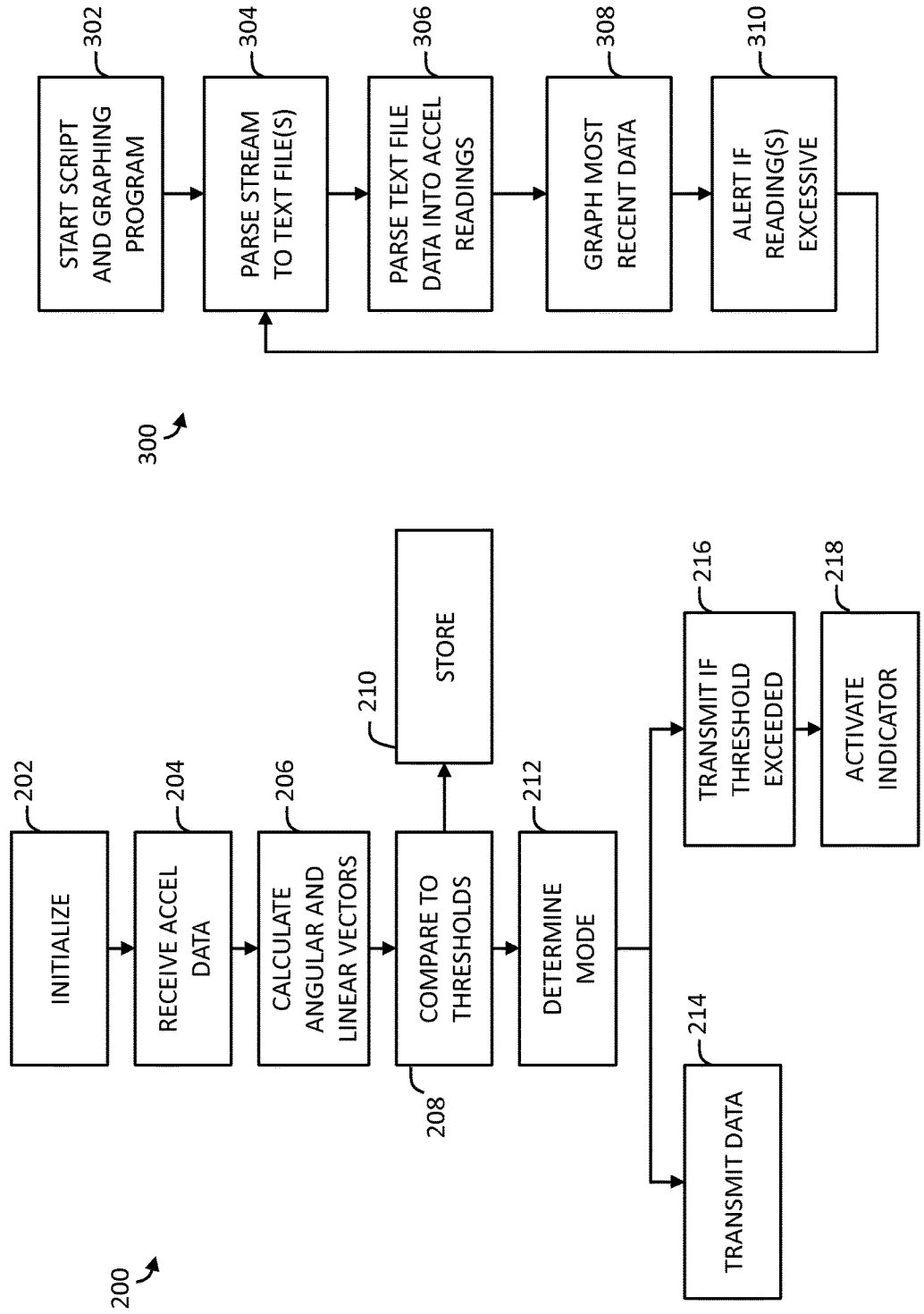
FIG. 6 is a flow chart of an illustrative method for processing data in a concussion data module.
FIG. 7 is a flow chart of an illustrative method for processing data in a base unit.

FIG. 6 is a block diagram of an illustrative method 200 for processing acceleration data in a concussion data module such as concussion data module 50 or 104. Method 200 may be implemented as computer program instructions or part of a computer program such as program 48, and may accordingly be executed by one or more processors onboard the concussion data module. Step 202 may include initialization of the concussion data module. For example, memory may be cleared, a geographic starting point may be set, thresholds may be set or adjusted, counters may be reset, and/or communication with a base unit may be established.

Step 204 may include receiving acceleration data from the accelerometers. For example, acceleration data may be received indicating acceleration on the x, y, and z axes for each of two accelerometers. This data may be received as it is generated by the accelerometers. In other examples, a frequency of data generation or reception may be user-adjustable.

Step 206 may include calculating linear and angular values for acceleration of the concussion data module. For example, a linear acceleration vector may be calculated for each of the accelerometers based on the axial data provided. Additionally, an angular or rotational vector for the concussion data module may be calculated based on data from the two accelerometers, as described above.

Step 208 may include comparing the vectorized acceleration values to thresholds. For example, each type of acceleration value may have one or more thresholds above which action should be taken. In some examples, both linear and angular acceleration may be compared to both a respective "mild" and "severe" limit or threshold. A mild limit may indicate a need for medical attention if it is repeatedly exceeded. Accordingly, a respective counter may be incremented each time a mild limit is exceeded, and a threshold or maximum allowable count may be set for the counter itself. A severe limit may indicate an immediate need for attention if exceeded even once.

Step 210 may include storing the raw data, calculated vector values, and/or any threshold comparison results in the onboard memory of the concussion data module. Other digital information may be stored with each data point, such as a time stamp or a device identifier. As described above, storage may be limited and may buffer in a FIFO manner.

Step 212 may include determining a mode of the concussion data module. For example, the processor may check the state of the mode selector switch or may instead check a persistent variable set by the mode selector switch or a virtual command. The selected mode may dictate what further actions are taken. For example, if the concussion data module is in a "transmit" mode, then step 214 may include transmitting the data and associated information to the base unit or other receiving device. If the concussion data module is in a "transmit on event" mode, then step 216 may include transmitting the data and associated information only if one or more thresholds have been exceeded. To allow a more complete analysis in such an event, the buffered contents of the memory may be transmitted as well. Step 218 may include activating one or more indicators such as a buzzer and/or a flashing light to indicate the threshold being exceeded.

FIG. 7 is a block diagram of an illustrative method 300 for processing incoming acceleration data from the concussion data modules at a base unit such as base unit 80 or 102. Method 300 may be implemented as computer program instructions or part of a computer program such as program 85 or 122, and may accordingly be executed by one or more processors associated with the base unit. Step 302 may include initiating the script or programs associated with carrying out following steps of method 300. For example, a shell script may be used to facilitate and coordinate execution of one or more other programs. In some examples, a Bash script may be used to coordinate additional steps, and a graphing program such as the free and open source LiveGraph software may be initiated as well to handle visualization of the incoming data.

Step 304 may include parsing the incoming data stream into appropriate text files. For example, each concussion data module may have a respective associated text file in memory in the base unit. Step 304 may include reading identifying information for each incoming data packet, and saving or writing the data to the appropriate text file in sequential fashion. The repeated application of this step as the process iterates may result in several text files, each of which includes an ordered list of the incoming data from an associated concussion data module.

Step 308 may include graphing or otherwise visualizing all or part of the received data. For example, a chart may be created to display acceleration values for one or more concussion data modules over time, with time units on the x axis of the chart and magnitude of acceleration on the y axis of the chart. If more than one concussion data module is associated with a single player-subject, a graph may be presented showing relative acceleration of the two or more concussion data modules on that subject.

Step 310 may include providing an alert if one or more thresholds have been exceeded. For example, a text message may be sent to all contacts on a contact list associated with a given concussion data module (and therefore a given player-subject), and/or a pop-up alert window may be presented in a GUI on a display associated with the base unit. In some examples, an alert may be displayed on a scoreboard, for example by indicating the jersey number of a player who has a concussion data module that has exceeded an acceleration threshold. Method 300 may continue to process incoming data by iterating through steps 304-310 as indicated in FIG. 7.

Figure 8:
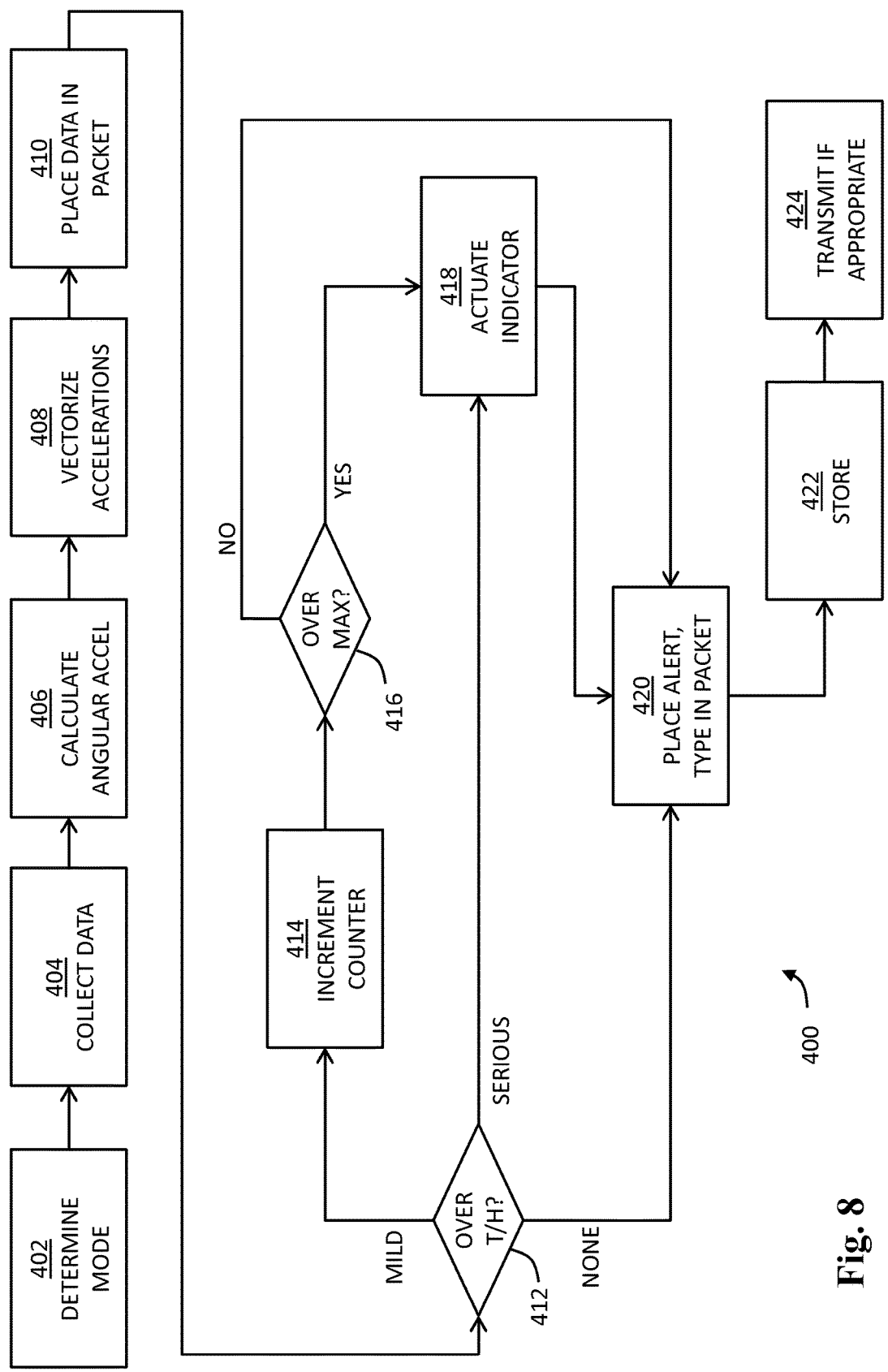
FIG. 8 is another illustrative method for processing data in a concussion data module.

FIG. 8 is a flow chart depicting an illustrative data processing method 400, similar to method 200, for execution in a concussion data module. Step 402 may include determining a mode of the concussion data module. As discussed above, this determination may include checking the status of a variable that is set by a mode selector switch and/or virtual command. Step 404 may include collecting data from the onboard accelerometers, which are in communication with the processing and memory unit on the concussion data module. Step 406 may include calculating angular acceleration based on the data collected from the two accelerometers as described above. Step 408 may include vectorizing the angular and linear acceleration of the concussion data module to produce a linear vector for each of the accelerometers and an angular vector for the concussion data module overall. Step 408 may include placing the raw data and/or the calculated vector values into a digital data packet. A data packet may include an ordered string of digital values. Each packet may include the data and calculations associated with one reading from each of the two accelerometers at one point in time. As such, a packet may include a time stamp from an onboard clock, a device identifier indicating the hardware source of the data, and/or any other information desired to be communicated to the base station. The contents of the packet are described further below regarding step 420.

Step 412 may include determining whether a threshold or limit has been exceeded by comparing the calculated values from step 408 to threshold values. For example, four acceleration thresholds may be defined and set either as hard limits or as user-adjustable limits: mild linear, severe linear, mild angular, and severe angular. If a mild threshold has been exceeded, step 414 may include incrementing a counter associated with the specific mild threshold. Step 416 may then include comparing the value of the incremented counter to a predetermined, possibly user-adjustable, count limit. For example, a count limit of four may be established, indicating that exceeding the specific mild threshold more than four times indicates a need for medical attention. If a count limit has been exceeded, or if a severe threshold has been exceeded in step 412, then step 418 may include activating one or more onboard indicators such as the audible or visual indicators previously described.

In any case, step 420 may include adding information to the data packet to indicate the specific result of the previous comparisons. For example, if a threshold has been exceeded, an alerting bit may be added to the packet. In some examples, an alerting bit may include adding a "+" to the front of the packet to indicate that a severe threshold has been exceeded. In some examples, an alerting bit may include adding a "−" to the front of the packet to indicate that a mild threshold has been exceeded. A bit may be added to the packet to indicate the acceleration type of threshold that has been exceeded. In some examples, an acceleration type bit may include adding an "R" to the end of the packet for a rotational or angular threshold, an "L" for linear, or an "N" for neither. In some examples, a "B" or some other suitable indicator may be used to indicate if both types of thresholds have been exceeded. In other examples, a priority may be established to determine what bits to indicate if more than one severity or more than one acceleration type has been exceeded. Similarly, other such indicators may be added to the packet to indicate that a count limit has been exceeded. In other examples, exceeding a count limit may be treated as a "severe" threshold and indicated accordingly.

Step 422 may include storing the resulting data packet in onboard storage, as described above. Step 424 may include transmitting the data packet based on the original assessment of the mode of the concussion data module. For example, the data packet may be transmitted only if a limit or threshold has been exceeded, in which case other contents of the memory may also be transmitted. On the other hand, a mode indicating constant transmission of data may transmit the packet on a scheduled or periodic basis, such as once per second. In that case, several packets may have accumulated and will be transmitted all at once. In other examples, each packet may be transmitted substantially immediately as it is produced by the processor.

FIG. 9 is a flow chart depicting an illustrative data transmission method 500 for execution in a concussion data module. If a concussion data module has determined that data should be transmitted, the data to be transmitted may first be prepared at least in part as described above regarding method 400. Step 502 may then include determining if the base unit is within the maximum effective range of the transmitter of the concussion data module. This may be accomplished, for example, by sending a test communication and receiving a return confirmation from the base unit that the test communication was received. In other examples, the base unit may periodically broadcast a signal that may be received by the concussion data modules, and a strength of that signal may be compared to a known value to determine the distance to the base unit and therefore whether the base unit is likely within range.

If the concussion data module is not within range to the base unit, step 504 may include transmitting a query to other concussion data modules. Any concussion data module that is within range to both the base unit and the originating concussion data module may then respond to indicate availability to relay communications as needed.

The originating concussion data module may then select a recipient in step 506 based on the previous determination. For example, if the base unit is within range, the base unit may be designated the recipient. If not, an available concussion data module that responded in step 504 may be selected. For example, the responding concussion data module with the strongest apparent signal strength may be chosen as the recipient. In other examples, the responding concussion data module indicating best signal strength with respect to the base unit may be chosen.

Step 508 may include adding header information to the packet or packets being sent. For example, a relay request and/or originating hardware identifier may be added. Step 510 may then include actually transmitting the packet or packets of data to the recipient.

FIG. 10 is a flow chart of another illustrative data transmission method 600 similar to method 500. As in step 502, step 602 may include determining if the base unit is within range. If the base unit is not in range, then unlike method 500, step 604 may include adding relay request information to the packet or packets to be transmitted. After adding header information in step 606 (similar to step 508) and transmitting in step 608, the broadcast packet or packets may be received by any concussion data module in range, and the relay request information may indicate to the receiving concussion data module that the data should be retransmitted to the base unit. In other words, method 600 involves broadcasting the data along with a request that it be retransmitted by any device that receives it, rather than first determining a suitable relay device and transmitting to that device only. In some examples, method 500 or method 600 may be employed. In other examples, method 500 may be executed first, followed by executing method 600 if no suitable relay device responds to the query of step 504.

FIG. 11 is a flow chart of an illustrative interrupt method 700 for handling relay of data in a concussion data module. Step 702 may include receiving inbound data from another concussion data module for retransmission. Each concussion data module may include a receiver for this purpose (among others), and may monitor for inbound data or commands. In some examples, this monitoring may include checking inbound communications for information indicating the communication is particularly for the receiving concussion data module. In some examples, monitoring may include checking inbound communications for generic requests for retransmission. In response to determining that data has been received and should be retransmitted, step 704 may include halting one or more existing processes and saving the state of the concussion data module in memory. Step 706 may include copying the received data to an outbound packet or packets, and step 708 may include copying the originating hardware identifier over as well. Step 710 may include transmitting the copied packet or packets to the base unit using a method such as method 500 or 600. Once transmission is in progress or complete, step 712 may include resuming any processes halted in step 704.

FIG. 12 is a block diagram of an illustrative method 800 for initializing a base unit such as base unit 80 or 102 in preparation for processing incoming acceleration data from the concussion data modules. Step 802 may include creating a master data folder in the digital file system of the base unit. The master data folder may contain all subsequent data received and processed by the base unit. Step 802 may also include prompting a user to activate or turn on each concussion data module to be used. Step 804 may include creating a subfolder within the master data folder for each concussion data module to be used. This may include establishing communication between each concussion data module and the base unit, and automatically creating a data subfolder for each concussion data module thus encountered. Any suitable naming convention may be used to name these subfolders. For example, a name for each subfolder may include a respective hardware identifier for the associated concussion data module. Note that in steps 802 and 804, the processor may first determine whether appropriate folders already exist, and may not create new folders if appropriate folders are found.

Step 806 may include prompting the user to input contact information for each concussion data module. For example, a cell phone number of a parent or parents of the player-subject associated with the concussion data module may be entered to indicate that a text message should be sent to that number in the event of a qualifying accelerative event. Certain blanket contact information may be entered to apply to all existing concussion data modules. For example, it may be desired that a coach or trainer be notified regardless of the concussion data module involved. Prompting the user in this step may include a dialog box or interactive text field(s) presented via a GUI on a display device.

Step 808 may include creating a respective working subfolder within each concussion data module subfolder for containing data from the current session. A name for each working subfolder may include the date and/or start time. Step 810 may include creating a suitable file such as a text file within each working folder for recording data received for the concussion data module. Once all concussion data modules have associated text files created, the base unit may indicate a readiness state to the user and/or to the concussion data modules.

Figure 13:
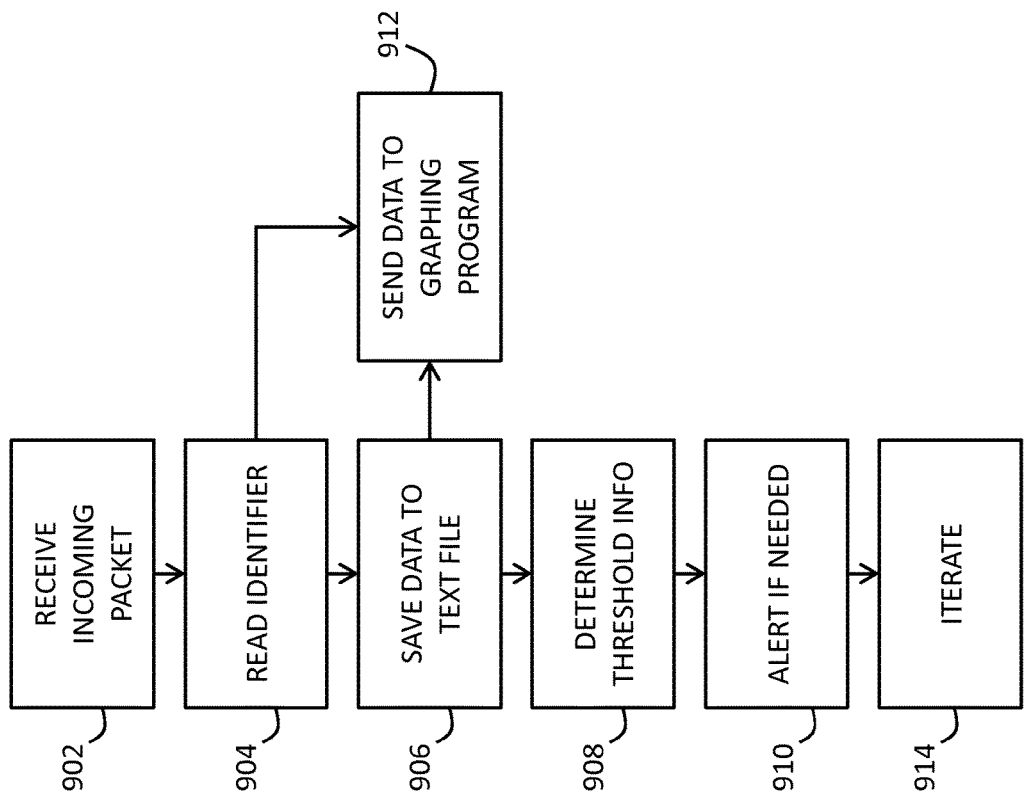
FIG. 13 is an illustrative method for processing data received by a base unit.

FIG. 13 is a block diagram of an illustrative method 900, similar to method 300, for processing incoming acceleration data from the concussion data modules at a base unit such as base unit 80 or 102. Method 300 may be implemented as computer program instructions or as part of a computer program such as program 85 or 122, and may accordingly be executed by one or more processors associated with the base unit. Step 902 may include receiving with the receiver of the base unit an incoming packet of data that was transmitted by a concussion data module. Step 904 may include reading the digital information contained in the transmission, and reading the hardware identifier associated with the data to determine the originating concussion data module. Step 906 may then save all or part of the data to the appropriate data/text file associated with that concussion data module.

Step 908 may include parsing the data to determine if any thresholds or limits were exceeded. For example, this may include reading the parts of the packet where alerting and acceleration type information were recorded by the concussion data module. If a limit or threshold has been exceeded, step 910 may include alerting the user and/or contacts that an event has occurred, what type of event occurred, and that further medical attention or evaluation may be needed. Alerts may include pop-up warnings on the display screen, text messages, displays of information on the scoreboard, audible alarms, flashing or constantly-lit lamps, prerecorded spoken messages, and the like. In some examples, a message or warning signal may be transmitted to the originating concussion data module to alert the player-subject either automatically or at the request of the user. Step 912 may include copying, sending, saving, and/or streaming incoming data to a related, connected, or stand-alone graphing program. The data may be sent to the graphing program at any point after it is received, synchronously or asynchronously. A graphing program may include any suitable software module or code configured to receive incoming data, parse the data if necessary, and present some or all of the data in a human-readable form such as graphically on a chart. As mentioned above, one suitable program for such a step may include LiveGraph. Step 914 may include iterating steps 902-912 as additional data is received. One skilled in the art will understand that two or more steps may be performed simultaneously or virtually simultaneously, and multiple data streams from multiple concussion data modules may be handled serially, in parallel, or in a threaded manner, as desired. One or more processors may execute these and other steps to facilitate the method.

The following examples may further illustrate various embodiments and features of concussion detection systems according to the present disclosure.

In a first example, a concussion detection and communication device may include a first electronic module capable of being mounted to a first sports helmet, the first electronic module including a controller, a transmit-receive assembly in communication with the controller, a first three-axis accelerometer and a second three-axis accelerometer each in communication with the controller and configured to communicate respective acceleration data to the controller, and a data storage unit in communication with the controller. The controller may be configured to generate digital data packets, and the data storage unit may be configured to store the digital data packets. Each digital data packet may contain information corresponding to the acceleration data from both of the first and second accelerometers at a certain time. The first electronic module may be operable in a first mode, in which the controller transmits via the transmit-receive assembly a first electromagnetic (EM) signal encoding at least one digital data packet associated with the first electronic module. The first electronic module may be operable in a second mode, in which the processor does not transmit digital data packets associated with the first data module. The transmit-receive assembly of the first electronic module may be capable of receiving a second EM signal transmitted by a second such electronic module, and the controller of the first electronic module may be configured to respond to the received second EM signal by retransmitting data contained in the second EM signal when the second EM signal contains information indicating a retransmission request.

The first accelerometer may be disposed at a fixed distance from the second accelerometer, and the controller may be further configured to calculate an angular acceleration of the first electronic module based at least in part on the fixed distance.

The controller may be further configured to use the respective acceleration data of the first and second accelerometers to determine a linear acceleration vector for each accelerometer at a certain time, to compare a magnitude of each resulting linear acceleration vector to a first threshold, and to include a result of the comparison in the digital data packet associated with said time.

The controller may be further configured to compare a magnitude of the angular acceleration at a certain time to a second threshold, and to include a result of the comparison with the second threshold in the digital data packet associated with said time.

The controller may be further configured to compare one of the linear acceleration values to a third threshold, and to increment a counter if said linear acceleration value exceeds the third threshold.

The controller may be configured to determine whether a base station is within range to receive the first EM signal.

The controller may be further configured to determine whether any other such electronic module is within range to receive the first EM signal.

The controller may be further configured to modify the first EM signal to include information indicating a retransmission request in response to a determination that the base station is not within range.

An illustrative concussion detection and communication system may include an electronic module associated with a first body part of a user and including a controller, a transmit-receive assembly in communication with the controller, a first three-axis accelerometer and a second three-axis accelerometer each in communication with the controller for communicating respective acceleration data to the controller, and a data storage unit in communication with the controller for storing information related to the acceleration data. The controller may be configured to receive the respective acceleration data from the first and second accelerometers, to calculate linear and angular acceleration values using the received data, to determine whether any calculated linear acceleration value exceeds a linear threshold value, and to determine whether any calculated rotational acceleration value exceeds a rotational threshold value. The electronic module may be operable in a first mode, in which the controller transmits via the transmit-receive assembly an electromagnetic (EM) signal containing information corresponding to the calculated acceleration values of the electronic module, and a second mode, in which the controller does not transmit a signal containing information corresponding to the calculated acceleration values of the electronic module. A base unit may be configured to receive the EM signal transmitted by the electronic module. The base unit may include a receiver configured to receive the EM signal, a processor in communication with the receiver and configured to extract data from the received EM signal, a memory in communication with the processor and configured to store the extracted data, and a display for presenting the extracted data in human-readable form. The electronic module may be configured to automatically enter the first mode in response to a determination by the controller that either or both of the linear and rotational threshold values has been exceeded.

The base unit may further include a transmitter capable of transmitting EM signals, wherein the electronic module may be configured to enter the first mode in response to receiving an EM signal transmitted by the base unit containing information indicating a mode request.

The electronic module may have a module identifier. The EM signal transmitted by the base unit may include a destination identifier. The electronic module may be configured to enter the first mode only if the destination identifier matches the module identifier.

The system may further include at least a second electronic module associated with a second user, the second electronic module being substantially identical to the first electronic module, wherein the module identifier of the first electronic module is different from the module identifier of the second electronic module.

Information corresponding to the respective module identifier of each electronic module may be included in the respective EM signal transmitted by each electronic module.

The system may further include a third electronic module associated with a second body part of the user, the third electronic module being substantially identical to the first electronic module.

The first body part may include a head of the user and the second body part may include a torso of the user. Each of the first and third electronic modules may be configured to transmit respective acceleration data to the base unit. The base unit may be configured to use the acceleration data from the first and third electronic modules to determine relative accelerations of the head and body of the user.

The electronic module may further include a clock in communication with the controller. The controller may be configured to associate a time signature from the clock with each of the calculated acceleration values.

Another example of a concussion detection and communication system may include a sports helmet configured to be worn on the head of a user. A concussion data module may be releasably mounted to the sports helmet, the concussion data module having two accelerometers for sensing acceleration of the module, a processor for processing acceleration data received from the accelerometers, a memory for storing the processed acceleration data, and a communication assembly including a receiver and a transmitter capable of communicating electromagnetic (EM) signals encoding the processed acceleration data. The processor may be configured to execute program instructions for processing the acceleration data, the processing including calculating a vectorized angular acceleration of the concussion data module, calculating a vectorized linear acceleration for each of the accelerometers, comparing the magnitude of the angular acceleration vector to a first threshold, comparing the magnitude of each of the linear acceleration vectors to a second threshold, collating the calculated vector data, results of the comparisons to the thresholds, a time value, and a device identifier into a data packet, storing the data packet in the memory, transmitting the data packet via the transmitter, and determining whether a responsive verification signal is received by the receiver, indicating that a receiving base unit is within communication range of the concussion data module.

The system may further include a second concussion data module substantially identical to the first concussion data module and releasably mounted to a sports helmet worn by a second user. The processor of the first concussion data module may be further configured to transmit the data packet to the second concussion data module in response to the first concussion data module determining that the receiving base unit is not within range.

The receiving base unit may be configured to receive the data packet transmitted by the concussion data module, and to provide an alert in response to determining from the data packet that one or more of the thresholds has been exceeded.

The alert may include a text message communicated to a cellular telephone.

Although the present disclosure has been provided with reference to the foregoing operational principles and embodiments, it will be apparent to those skilled in the art that various changes in form and detail may be made without departing from the spirit and scope of the disclosure. The present disclosure is intended to embrace all such alternatives, modifications and variances. Where the disclosure recites "a," "a first," or "another" element, or the equivalent thereof, it should be interpreted to include one or more such elements, neither requiring nor excluding two or more such elements. Furthermore, any aspect shown or described with reference to a particular embodiment should be interpreted to be compatible with any other embodiment, alternative, modification, or variation.

What is claimed is:

1. A device comprising:
   a first electronic module capable of being mounted to a sports helmet, the first electronic module including a controller, a transmit-receive assembly in communication with the controller, a first three-axis accelerometer and a second three-axis accelerometer each in communication with the controller and configured to communicate respective acceleration data to the controller at a first rate, and a data storage unit in communication with the controller;
   the controller being configured to generate digital data packets, and the data storage unit being configured to store the digital data packets, each digital data packet containing information corresponding to the acceleration data from both of the first and second accelerometers at a certain time, as communicated to the controller at the first rate;
   the first electronic module being operable in a first mode, in which the controller transmits, at a second rate lower than the first rate, via the transmit-receive assembly a first electromagnetic (EM) signal containing at least a first digital data packet associated with the first electronic module, and a second mode, in which the processor does not transmit digital data packets associated with the first data module;
   wherein the transmit-receive assembly of the first electronic module is configured to receive a second EM signal containing a second digital data packet transmitted by a second electronic module substantially identical to the first electronic module, and the controller of the first electronic module is configured to respond to the received second EM signal by retransmitting data contained in the second digital data packet when the second digital data packet contains information indicating a request to retransmit the second digital data packet; and
   a base unit configured to receive the first EM signal transmitted by the first electronic module, the base unit including a receiver configured to receive the first EM signal, a processor in communication with the receiver and configured to extract acceleration data from the received first EM signal, a memory in communication with the processor and configured to store the extracted acceleration data, the extracted acceleration data having a number of data points corresponding to the first rate, and a display for presenting the extracted acceleration data in human-readable form, the base unit further configured to recreate, based on the extracted acceleration data, a path over time taken by the first electronic module.

2. The device of claim 1, wherein the first accelerometer is disposed at a fixed distance from the second accelerometer, and the controller is further configured to calculate an angular acceleration of the first electronic module based at least in part on the fixed distance.

3. The device of claim 2, wherein the controller is further configured to use the respective acceleration data of the first and second accelerometers to determine a linear acceleration vector for each accelerometer at a certain time, to compare a magnitude of each resulting linear acceleration vector to a first threshold, and to include a result of the comparison in the digital data packet associated with said time.

4. The device of claim 3, wherein the controller is further configured to compare a magnitude of the angular acceleration at a certain time to a second threshold, and to include a result of the comparison with the second threshold in the digital data packet associated with said time.

5. The device of claim 3, wherein the controller is further configured to compare one of the linear acceleration values to a third threshold, and to increment a counter if said linear acceleration value exceeds the third threshold.

6. The device of claim 1, wherein the controller is configured to determine whether a base station is within range to receive the first EM signal.

7. The device of claim 6, wherein the controller is further configured to determine whether any other such electronic module is within range to receive the first EM signal.

8. The device of claim 6, further including a third electronic module substantially identical to the first and second electronic modules, wherein the controller is further configured, in response to a determination that the base station is not within range, to modify the first data packet to include information indicating a request for the third electronic module to retransmit the first digital data packet.

9. A system comprising:
a first electronic module associated with a first body part of a user and including a controller, a transmit-receive assembly in communication with the controller, a first three-axis accelerometer and a second three-axis accelerometer each in communication with the controller for communicating respective acceleration data to the controller at a first rate, and a data storage unit in communication with the controller for storing information related to the acceleration data;
the controller being configured to receive the respective acceleration data from the first and second accelerometers, to calculate linear and rotational acceleration values using the received data, to determine whether any calculated linear acceleration value exceeds a linear threshold value, and to determine whether any calculated rotational acceleration value exceeds a rotational threshold value;
the first electronic module being operable in a first mode, in which the controller transmits, at a second rate lower than the first rate, via the transmit-receive assembly an electromagnetic (EM) signal containing information corresponding to the calculated acceleration values of the first electronic module, and a second mode, in which the controller does not transmit a signal containing information corresponding to the calculated acceleration values of the first electronic module; and
wherein the transmit-receive assembly of the first electronic module is configured to receive a second EM signal containing a second digital data packet transmitted by a second electronic module substantially identical to the first electronic module, and the controller of the first electronic module is configured to respond to the received second EM signal by retransmitting data contained in the second digital data packet when the second digital data packet contains information indicating a request to retransmit the second digital data packet; and
a base unit configured to receive the EM signal transmitted by the first electronic module, the base unit including a receiver configured to receive the EM signal, a processor in communication with the receiver and configured to extract data from the received EM signal, a memory in communication with the processor and configured to store the extracted data, and a display for presenting the extracted data in human-readable form, the base unit further configured to recreate, based on the calculated acceleration values of the first electronic module, a path over time taken by the user;
wherein the first electronic module is configured to automatically enter the first mode in response to a determination by the controller that either or both of the linear and rotational threshold values has been exceeded.

10. The system of claim 9, the base unit further including a transmitter capable of transmitting EM signals, wherein the first electronic module is configured to enter the first mode in response to receiving an EM signal transmitted by the base unit containing information indicating a mode request.

11. The system of claim 10, wherein the first electronic module has a module identifier, the EM signal transmitted by the base unit includes a destination identifier, and the first electronic module is configured to enter the first mode only if the destination identifier matches the module identifier.

12. The system of claim 11, wherein the system further including the first electronic module associated with a first user, the second electronic module associated with a second user, the second electronic module being substantially identical to the first electronic module, wherein the module identifier of the first electronic module is different from the module identifier of the second electronic module.

13. The system of claim 12, wherein information corresponding to the respective module identifier of each electronic module is included in the respective EM signal transmitted by each electronic module.

14. The system of claim 9, wherein the system further including a third electronic module associated with a second body part of the user, the third electronic module being substantially identical to the first electronic module.

15. The system of claim 14, wherein the first body part comprises a head of the user and the second body part comprises a torso of the user, each of the first and third electronic modules being configured to transmit respective acceleration data to the base unit, and the base unit configured to use the acceleration data from the first and third electronic modules to determine relative accelerations of the head and body of the user.

16. The system of claim 9, each electronic module further including a clock in communication with the controller, the controller configured to associate a time signature from the clock with each of the calculated acceleration values.

17. A system for processing acceleration data associated with a head of a user, the system comprising:
a sports helmet configured to be worn on the head of the user;
a concussion data module releasably mounted to the sports helmet, the concussion data module having two accelerometers for sensing acceleration of the module and having a rate of data output, a processor for processing acceleration data received from the accelerometers at the rate of data output, a memory for storing the processed acceleration data, and a communication assembly including a receiver and a transmitter capable of communicating electromagnetic (EM) signals encoded using the processed acceleration data; and wherein the user is a first user and the concussion data module is a first concussion data module, the system further including a second concussion data module substantially identical to the first concussion data module and releasably mounted to a sports helmet worn by the second user, and wherein the processor of the first concussion data module is further configured to transmit the data packet to the second concussion data module in response to the first concussion data module determining that the receiving base unit is not within range; and a base unit configured to receive EM signals from the transmitter of the concussion data module;

wherein the processor of the concussion data module is configured to execute program instructions for processing the acceleration data, the processing including repeatedly:

calculating a vectorized angular acceleration of the concussion data module, calculating a vectorized linear acceleration for each of the accelerometers, comparing the magnitude of the angular acceleration vector to a first threshold, comparing the magnitude of each of the linear acceleration vectors to a second threshold, collating the calculated vector data, results of the comparisons to the thresholds, a time value, and a device identifier into a data packet, storing the data packet in the memory, transmitting the data packet via the transmitter, and determining whether a responsive verification signal is received by the receiver of the concussion data module, indicating that the base unit is within communication range of the concussion data module; and wherein the base unit is configured to store a plurality of the data packets repeatedly transmitted by the concussion data module, to extract the acceleration data therefrom, and to recreate, based on the extracted acceleration data, a path over time taken by the user.

18. The system of claim 17, wherein the receiving base unit is configured to provide an alert in response to determining from the data packet that one or more of the thresholds has been exceeded.

19. The system of claim 18, wherein the alert includes a text message to a cellular telephone.

20. The system of claim 1, wherein the first rate is at least approximately one thousand times per second.

* * * * *